(12) United States Patent
Rosenquist (10) Patent No.: US 9,968,770 B2
(45) Date of Patent: May 15, 2018

(54) ARRANGEMENT IN A MEDICAL CONNECTOR DEVICE

(75) Inventor: Tobias Rosenquist, Kallered (SE)

(73) Assignee: Carmel Pharma AB, Gothenburg (SE)

( * ) Notice: Subject to any disclaimer, the term of this patent is extended or adjusted under 35 U.S.C. 154(b) by 797 days.

(21) Appl. No.: 14/401,771

(22) PCT Filed: May 21, 2012

(86) PCT No.: PCT/SE2012/050545
§ 371 (c)(1),
(2), (4) Date: Apr. 8, 2015

(87) PCT Pub. No.: WO2013/176586
PCT Pub. Date: Nov. 28, 2013

(65) Prior Publication Data
US 2015/0209568 A1    Jul. 30, 2015

(51) Int. Cl.
B65B 1/04      (2006.01)
A61M 39/10    (2006.01)
A61M 39/16    (2006.01)

(52) U.S. Cl.
CPC ............ *A61M 39/10* (2013.01); *A61M 39/16* (2013.01); *A61M 39/1011* (2013.01); *A61M 2039/1033* (2013.01); *A61M 2039/1072* (2013.01); *F04C 2270/0421* (2013.01)

(58) Field of Classification Search
CPC .................. A61M 39/10; A61M 39/16; A61M 2039/1033; A61M 2039/1072; A61M 39/1011; F04C 2270/0421
See application file for complete search history.

(56) References Cited

U.S. PATENT DOCUMENTS

| 4,564,054 A | 1/1986 | Gustavsson |
| 4,895,570 A | 1/1990 | Larkin |
| 5,122,123 A | 6/1992 | Vaillancourt |
| 5,545,152 A | 8/1996 | Funderbuck et al. |
| 5,555,908 A | 9/1996 | Edwards et al. |
| 6,626,418 B2 | 9/2003 | Kiehne |
| 7,040,598 B2 | 5/2006 | Raybuck |

(Continued)

FOREIGN PATENT DOCUMENTS

| CN | 102458342 A | 5/2012 |
| JP | 5200098 A | 8/1993 |

(Continued)

*Primary Examiner* — Jason K Niesz
(74) *Attorney, Agent, or Firm* — The Webb Law Firm (57) ABSTRACT

A medical transfer and connecting device (1) for connecting a first medical appliance with a second medical appliance, the device having an axial direction (A) and a radial direction (R) and comprising an outer part (2) having a first end (8) and a second end (9) with an end opening (10) and a bore (4) extending in the axial direction (A) between the first (8) end and the second end (9). An inner part (3) carrying a barrier member (12) and having a central canal (7) extends in the axial direction (A) and is telescopically arranged in the bore (4) in the outer part (2), the inner part (3) with the barrier member (12) being axially movable in the bore (4) in the outer part (2) between a shielding position in which the barrier member (12) is completely located within the bore (4) in the outer part (2) and a cleaning position in which the barrier member (12) is located with at least a portion of the barrier member (12) extending axially past the end opening (10) in the outer part (2).

13 Claims, 5 Drawing Sheets

(56) References Cited

U.S. PATENT DOCUMENTS

| | | |
|---|---|---|
| 8,721,614 B2 | 5/2014 | Takemoto et al. |
| 2002/0002351 A1 | 1/2002 | Cote, Sr. et al. |
| 2003/0060804 A1 | 3/2003 | Vaillancourt |
| 2006/0106349 A1 | 5/2006 | Kito et al. |
| 2006/0161115 A1 | 7/2006 | Fangrow |
| 2008/0287920 A1 | 11/2008 | Fangrow et al. |
| 2010/0249724 A1 | 9/2010 | Cote, Sr. et al. |
| 2011/0284561 A1 | 11/2011 | Rosenquist et al. |
| 2012/0209218 A1 | 8/2012 | Ohlin et al. |

FOREIGN PATENT DOCUMENTS

| | | |
|---|---|---|
| JP | 2001505102 A | 4/2001 |
| JP | 2001506156 A | 5/2001 |
| JP | 2004160206 A | 6/2004 |
| JP | 2008518719 A | 6/2008 |
| JP | 201125066 A | 2/2011 |
| WO | 9826835 A1 | 6/1998 |
| WO | 2011052481 A1 | 5/2011 |

ARRANGEMENT IN A MEDICAL CONNECTOR DEVICE

CROSS-REFERENCE TO RELATED APPLICATIONS

This application is the United States national phase of International Application No. PCT/SE2012/050545 filed May 21, 2012, the disclosure of which is hereby incorporated in its entirety by reference.

TECHNICAL FIELD

The invention pertains to a protective connecting device for connecting a first medical appliance with a second medical appliance under hygienic and safe conditions.

BACKGROUND OF THE INVENTION

A major problem in relation to drug preparation, drug administration or other similar handling of pharmaceuticals is the risk of medical and pharmacological staff being exposed to drugs or solvents which may escape into ambient air. The problem is particularly serious when cytotoxins, antiviral drugs, antibiotics and radiopharmaceuticals are concerned. Other hazards may arise when taking samples relating to virus infections or the like.

Some drugs must be dissolved or diluted before they are administered, which involves transferring a solvent from one container to a sealed vial containing the drug in powder or liquid form, by means of a needle for example. Drugs may be inadvertently released into the atmosphere in gas form or by way of aerosolization, during the withdrawal of the needle from the vial and while the needle is inside the vial if any pressure differential between the interior of the vial and surrounding atmosphere exists.

For these reasons, systems for handling and administrating drugs and other medical substances under improved safety conditions have been developed.

U.S. Pat. No. 4,564,054 (Gustavsson) discloses a fluid transfer device for preventing air contamination when transferring a substance from one vessel to a second vessel. The device is attached or connectible to the vessel and comprises a first member, in which a piercing member such as a hollow needle is enclosed. The first member has a sealing member through which the needle can be passed. The device further comprises a second member, which is detachably connectable to the first member and which also comes a sealing member. When the first and second members are connected to each other, the two sealing members are located in a position with respect to each other so that they can be penetrated by the piercing member which is movable with respect to the sealing member.

The sealing members used in the high-security transfer and connecting devices disclosed herein are flexible and elastically compressible liquid and gas-proof membranes, also known as barriers or septums which have the ability of sealing tightly after penetration and retraction of a piercing member in order to prevent escape of liquid as well as gas components.

Commonly used sealing members are made from a thermoplastic elastomeric polymer material (TPE) allowing the members to be affixed in a connecting device by thermal welding, such as ultrasonic welding.

The medical transfer and connecting devices are designed for repeated and intermittent, use, for example when removing individual doses of a pharmaceutical from a vial or when connecting an injection device to a catheter, IV-equipment, or similar. It is not uncommon that each transfer and connecting device is used many times, such as up to 10 times, before eventually being discarded or replaced. After use, the device may often be left with the sealing member exposed to the environment for several hours before the next instance of use. The connecting devices are used in non-aseptic environments and in environments where the risk of contamination with bacteria and other hazardous matter may be high such as in hospital wards. As the connecting devices may be used for a long time under such conditions, a risk for bacterial growth on the sealing member is imminent. Accordingly, it is highly desirable that the device and in particular the sealing member, in the device be cleaned before each new use, in particular if a longer time period has lapsed since the last use. Without adequate cleaning of the sealing member before use, there is a risk that bacteria enters into the medical transfer system and is eventually transferred to a patient causing suffering and increased medical expenses.

Accordingly, there is a need for a medical transfer and connecting device for use in medical equipment involving handling of fluids such as pharmaceuticals, which transfer and connecting device can be easily and efficiently cleaned.

SUMMARY OF THE INVENTION

In accordance with the invention there is offered a medical transfer and connecting device for connecting a first medical appliance with a second medical appliance, the device having an axial direction and a radial direction and comprising an outer part having a first end and a second end with an end opening and a bore extending in the axial direction between the first end and the second end and wherein an inner part carrying a barrier member and having a central canal extending in the axial direction is telescopically arranged in the bore in the outer part, the inner part with the barrier member being axially movable in the bore in the outer part between a shielding position in which the barrier member is completely located within the bore in the outer part and a cleaning position in which the barrier member is located with at least a portion of the barrier member extending axially past the end opening in the outer part.

In the shielding position, the inner part of the transfer and connecting device is completely located inside the outer part and the barrier-member is radially shielded by the outer part. In the cleaning position, the barrier member protrudes out from the outer part of the transfer and connecting device and is readily accessible for cleaning. After cleaning, the inner part can be retracted into the outer part of the transfer and connecting device, whereby the transfer and connecting device is made ready for use and the barrier member can be safely and hygienically pierced by a piercing member. During use of the device for transferring a substance between two medical devices, the outer part serves to protect the barrier member and the piercing site from contamination and forms a stabilizing connection or support for the medical device carrying the piercing member. The central canal in the inner part of the device allows a piercing member from a first medical device to pass through the transfer and connecting device and serves to guide and shield the piercing member when it is inserted into a second medical device for removal of a fluid from or delivering a fluid into the second medical device.

Accordingly, in accordance with the invention the inner part and the outer part of the transfer and connecting device can be moved with respect to each other so that the barrier member on the inner part can be moved to a position where it can be easily cleaned. In transfer and connecting devices known in the art, cleaning of the barrier member is performed by using a cotton tip to reach the barrier member inside the transfer and connecting device. It is difficult to reach and efficiently clean all exposed parts of the barrier member as it is located in a fixed position inside the transfer and connecting device. With a transfer and connecting device in accordance with the invention, the barrier member can be quickly and adequately cleaned by simple wiping when the barrier member has been brought into the cleaning position.

The relative telescopic movement of the outer part and the inner part of the transfer and connecting device according to the invention may be accomplished in any suitable manner.

For instance, the outer part of the device may comprise at least one axially extending groove and the inner part may comprise corresponding means for sliding engagement with the at least one groove in the outer part.

The means for sliding engagement with the at least one groove may comprise a spring strut, a knob, a ridge, or similar element protruding from the inner part.

When the means for sliding engagement with a groove in the outer part comprised a spring strut, the spring strut may extend towards the second end of the inner part, and may be slightly outwardly inclined with respect to a central axis through the transfer and connecting device. It may be preferred that at least two spring struts are arranged on the inner part of the transfer and connecting device. If more than one spring strut is being used, they are preferably symmetrically arranged on the inner part. For example, two spring struts are preferably arranged diametrically opposite each other on the inner part.

The means for sliding engagement with said at least one groove may comprise one or more lugs. The one or more lugs may be used in addition to or instead of one or more spring struts.

The groove in the outer part and the lug may be configured to form a bayonet fitting between the outer part and the inner part of the transfer and connecting device.

The transfer and connecting device may comprise means for releasably locking the inner part in the shielding position. Furthermore, the transfer and connecting device may comprise means for releasably locking the inner part in the cleaning position. The locking means may be a bayonet fitting, or a stopping element arranged in the bore in the outer part such as a stop notch, a stop knob, a snap lock, etc. as known in the art.

The transfer and connecting device may comprise means for connecting the device to a first medical device, such as a medical vial, a catheter or similar.

The transfer and connecting device may comprise connecting means for connecting the device to a second medical device, the second medical device comprising a piercing member.

Definitions

By a "sterilized" or "sterile" device is meant a device that has been subjected to a sterilization method to remove viable micro-organisms, which method is accepted for the current product by the relevant authority. Current regulations in Europe for medical devices to be designated "STERILE" may be found in the European standard EN 556-1. Other regulations may exist in other countries. The sterilization can be ethylene oxide sterilization, sterilisation by irradiation, or (moist) heat sterilization or any other accepted method. The European standard requirements imply that the theoretical probability of there being a viable micro-organism present on/in the sterilized device shall be equal to or less than $1 \times 10^{-6}$.

The barrier members in the transfer and connecting device of the invention are made of materials that are referred to as being "flexible", "expandable" and "compressible". As used in this document these expressions are intended to mean materials that are capable of being elastically flexed, expanded or compressed under the influence of external forces arid that will substantially return to their original state once the external forces are removed. A "flexible material" is intended to mean a material that can easily be folded or twisted or bent by hand or a material that may be flexed and/or bent repeatedly without rupture or the development of visible defects in accordance with the definition in ISO 472:1999 "Plastics—Vocabulary".

By "elastomer" as used herein is implied a macromolecular material which returns rapidly to its initial dimension and shape after substantial deformation by a weak stress and release of the stress. The definition applies under room temperature test conditions and is found in ISO 472:1999.

The parts of the transfer and connecting device may be molded from comparatively rigid plastic as is known in the art. A rigid plastic material for the purpose of the invention is a material that will retain its shape during normal use and that will not be flexed or deformed by the forces required to manipulate the transfer and connecting device between the shielding position and the cleaning position or by the forces required to connect the device to first and second medical devices. However, the rigid plastic materials that are useful in a transfer and connecting device according to the invention preferably have the ability to elastically flex and deform under greater forces such as the forces arising during assembly of the transfer and connecting device.

BRIEF DESCRIPTION OF THE DRAWINGS

The invention will be described in greater detail with reference to the appended drawings in which.

DETAILED DESCRIPTION

The medical transfer and connecting device 1 that is shown in FIGS. 1-9 has a generally elongate tubular shape and comprises an outer part 2 and an inner part 3 which are telescopically arranged with the inner part 3 inserted in a central bore 4 in the outer part 2. The transfer and connecting device 1 has an axial direction A and a radial direction R perpendicular to the axial direction A. The inner part 3 has a first end 5 and a second end 6 and a central through-going, canal 7 extending in the axial direction A and being concentrically arranged in the central bore 4 in the outer part 2. The outer part 2 has a first end 8 and a second end 9 with an end opening 10 with the central bore 4 extending between the first end 8 and the second end 9. The central canal 7 in the inner part 3 is arranged to guide and protect a piercing member on a medical device positioned at the second end 9 of the outer part 2 during insertion of the piercing member into another medical device located at the first end 8 of the outer part 2.

Figure 6:
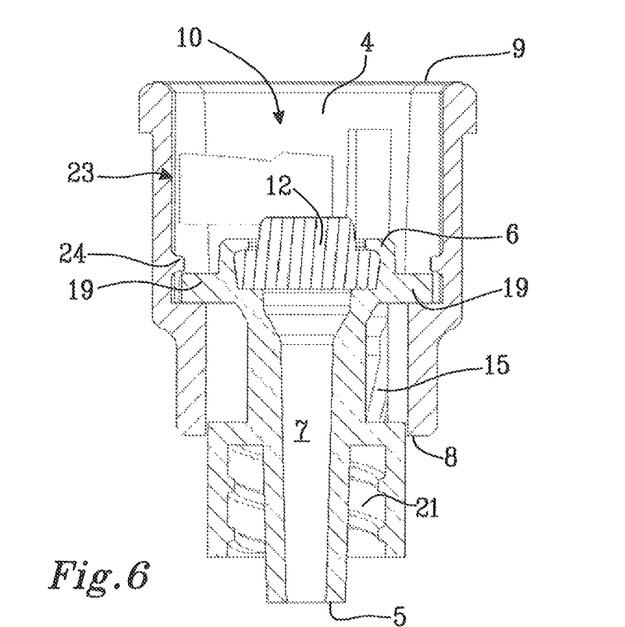
FIG. 6 shows a cross-sectional view of the transfer and connecting device in FIG. 1 taken along, the line VI-VI in FIG. 2.
Figure 7:
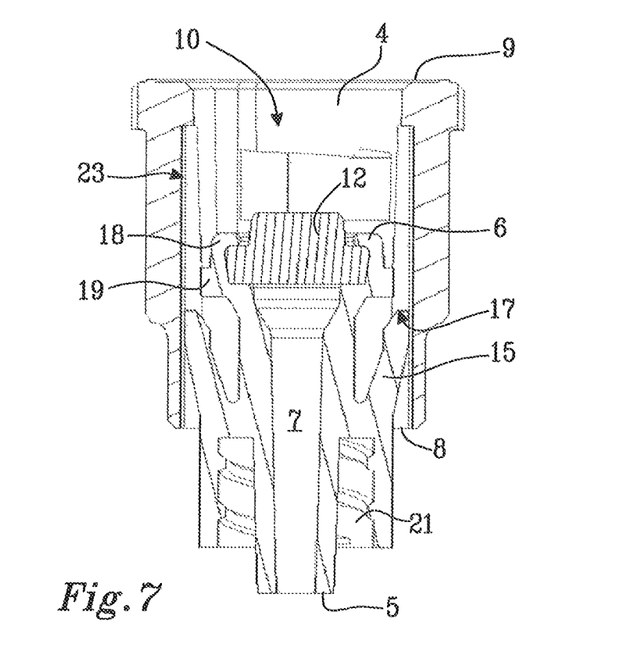
FIG. 7 shows a cross-sectional view of the transfer and connecting device in FIG. 1 taken along the line VII-VII in FIG. 2.

The inner part 3 carries a barrier member 12 which is applied over and seals the central canal 7 in the inner part 3 at the second end 6 of the inner part 3 as best seen in FIGS. 6 and 7. The barrier member is a flexible. elastically compressible membrane or septum, as disclosed herein and serves to form a barrier against unwanted transfer of substances from one side of the barrier member 12 to the opposite side of the barrier member 12 and ascertains a hygienic and safe connection between two medical devices. The barrier members of the invention may be made from medical grade elastomeric polymer materials as known in the art. Such materials include silicone elastomers, natural elastomer and thermoplastic elastomeric polymer materials (TPE). Thermoplastic elastomers include Styrene Block Copolymers (TPS), Thermoplastic Polyolefins (TPO), Thermoplastic polyurethanes (TPU), copolyesters and polyether block amides.

Figure 2:
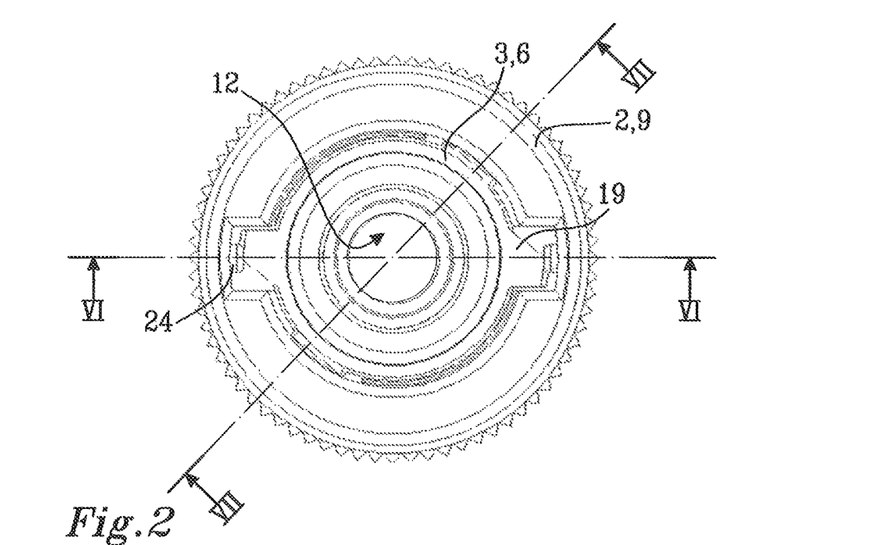
FIG. 2 shows an end view of the transfer and connecting device in FIG. 1.
Figure 3:
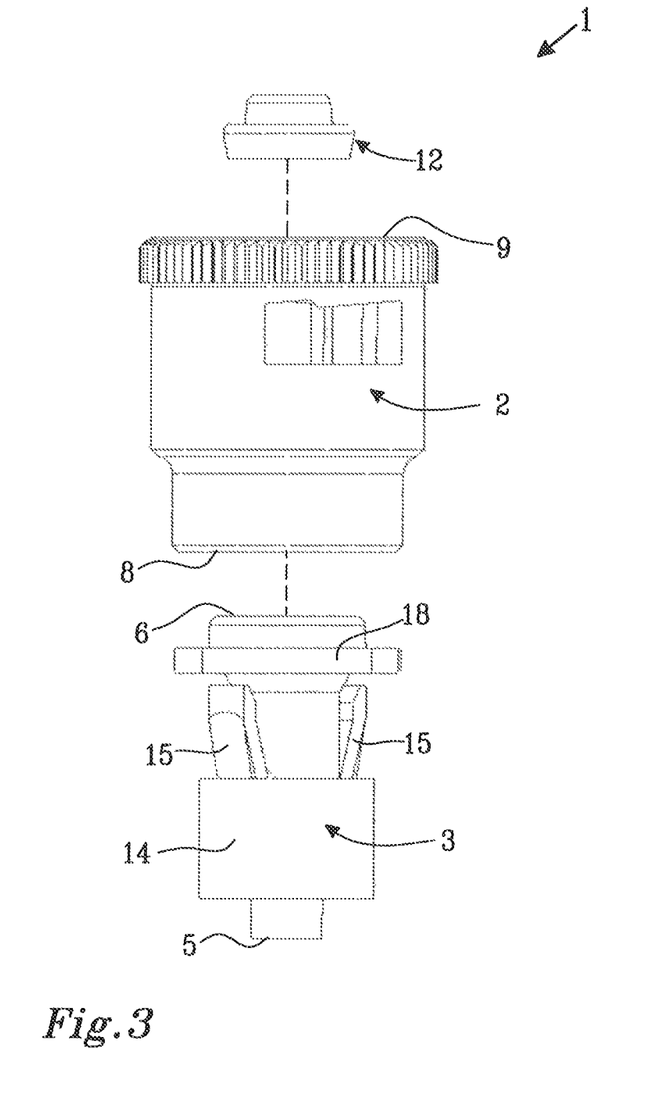
FIG. 3 shows an exploded view of the transfer and connecting device in FIG. 1.
Figure 5:
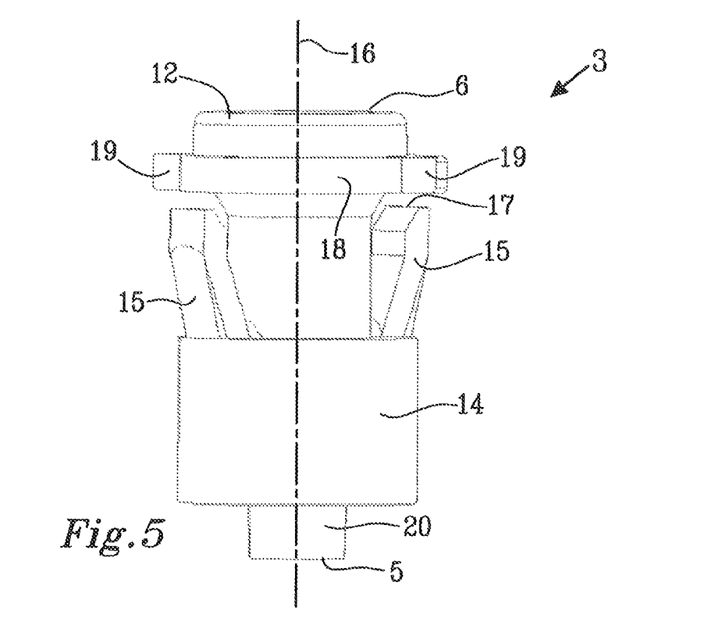
FIG. 5 shows a side view of an inner part of the transfer and connecting device in FIG. 1.

With particular reference to FIGS. 2 and 3 and 5, the inner part 3 comprises a cylindrical body 14 having two spring struts 15 extending towards the second end of the inner part 3 and being slightly outwardly inclined with respect to a central axis 16 through the transfer and connecting device 1. The spring struts 15 are arranged diametrically opposite each other and each terminates in a free end having an abutting surface 17 arranged to cooperate with a corresponding abutting surface on the outer part 2 of the transfer and connecting device 1. The spring struts 15 serve both as locking members and guiding elements and may be substituted with other means performing, these functions as disclosed herein. The functions of the spring struts may also be performed separately by using, different locking and guiding elements. Although it may be preferred to use two spring struts arranged opposite each other, it is conceivable to use only one spring strut. If more than one spring strut is being used, the spring struts are preferably symmetrically arranged on the inner part.

A barrier member holder 18 is arranged at the second end 6 of the inner part 3. Resilient barrier members are commonly made from a thermoplastic elastomeric polymer material (TPE) allowing the members to be affixed in the barrier member holder by ultrasonic welding. However, other types of medical grade elastomeric materials may be used and the barrier member may be attached to the inner part by any means known to the person skilled in the art. The barrier member holder 18 carries the barrier member 12 and is further provided with two radially opposing lugs 19 arranged to cooperate with corresponding grooves in the outer part 2 of the transfer and connecting device 1.

The first end 5 of the inner part 3 is provided with a male connector 20 extending out of the cylindrical body 14 of the inner part 3. The inside of the cylindrical body 14 of the inner part 3 has an inner thread 21. The male connector and the inner thread constitute means for connecting with a mating medical device such as a catheter or similar. The specific connecting means showed herein should not be considered limiting to the invention and it is to be understood that other connecting means may be used depending on the medical device to which the transfer and connecting device is to be fitted.

Figure 4:
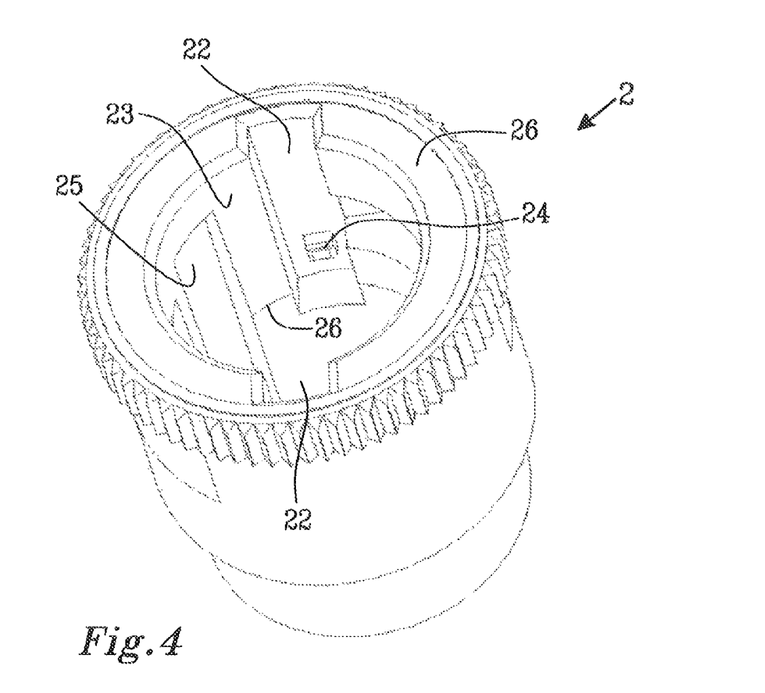
FIG. 4 shows a perspective view of an outer part of the transfer and connecting device in FIG. 1.

As is shown in FIG. 4, the outer part 2 of the transfer and connecting device 1 comprises opposing grooves 22 formed in the inner wall 23 of the outer part 2 and being arranged to form a bayonet fitting with the corresponding lugs 19 on the inner part 3. A locking knob 24 is arranged on the inner wall of the outer part 2 to keep the inner part 3 releasably locked in a shielding position in the outer part 2. Guiding tracks 25 for cooperating with the spring struts 15 on the inner part 3 of the transfer and connecting device 1 are also arranged in the axial direction of the outer part 2. Alternative couplings between the outer part 2 and the inner part 3 may be used within the scope of the invention, such as threaded couplings, etc. Furthermore, the locking knob 24 may be substituted by another locking element, such as an elastically flexible locking tongue arranged in the wall of the outer part 2.

Figure 8:
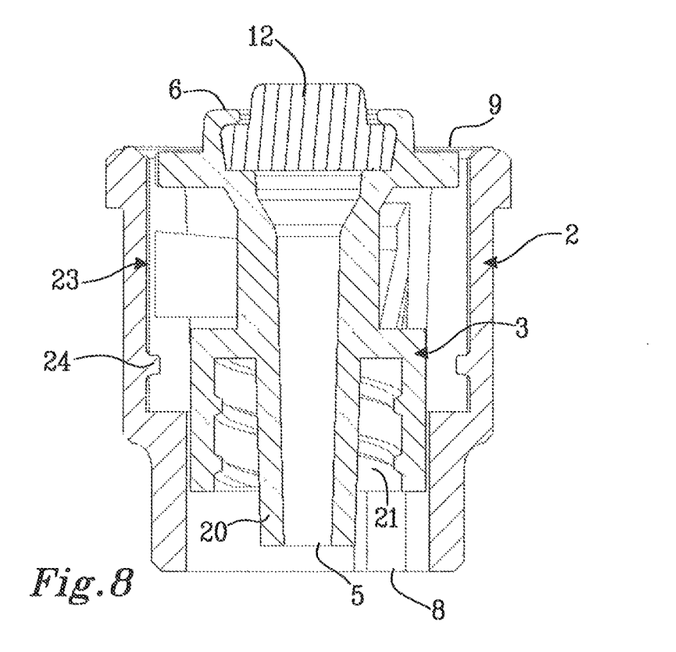
FIG. 8 shows a cross-sectional view of the transfer and connecting device in FIG. 1 in a cleaning position taken along the line VI-VI in FIG. 2.
Figure 9:
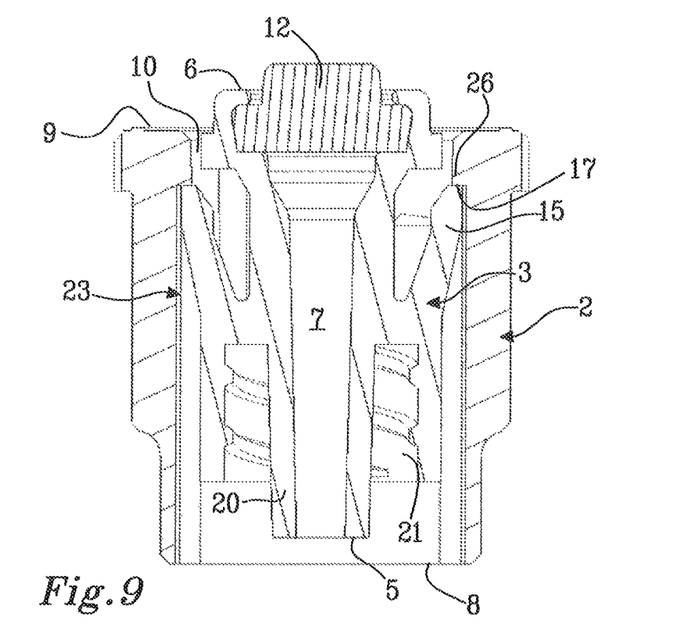
FIG. 9 shows a cross-sectional view of the transfer and connecting device in FIG. 1 in a cleaning position taken along the line VII-VII in FIG. 2.

The spring struts 15 on the inner part 3 may be bent slightly inwardly in the radial direction R when being inwardly pressed. Although other configurations of guiding elements and locking means than those disclosed herein are contemplated within the scope of the invention, the spring struts 15 disclosed herein have the advantage that they allow the transfer and connecting device 1 to be easily assembled by pressing the inner part 3 into the central bore 4 of the outer part 2 from the end opening 10 at the second end 9 of the outer part 2. The inner part 3 is pushed into the outer part 2 until the spring struts 15 pass a locking rim 26 in the wall 23 of the outer part 2. As the inner part 3 moves into the outer part 2, the spring struts 15 are initially pressed together in the radial direction causing them to bend slightly in order to fit in the central bore 4 of the outer part 2. The inclined configuration of the spring struts 15 helps guiding the inner part 2 into the outer part 3. Once pushed into place inside the outer part 2, the inner part 3 is prohibited from falling out of the outer part 3 by the spring struts 15 springing back to a relaxed non-tensioned position with the abutting surfaces 17 of the spring struts 15 located beneath the locking rim 26 on the outer part 2. A situation where the spring struts 15 are located in a position immediately beneath the locking rim 26 is best illustrated in FIG. 9 which shows the inner part 3 being arranged with the second end 6 positioned at the second end 9 of the outer part 2 such that the barrier member 12 protrudes out of the end opening 10 at the mouth of the central bore 4 in the outer part 2. The location of the inner part 3 in the outer part 2 as shown in FIGS. 8 and 9 corresponds to a cleaning position for the transfer and connecting device 1.

Figure 1:
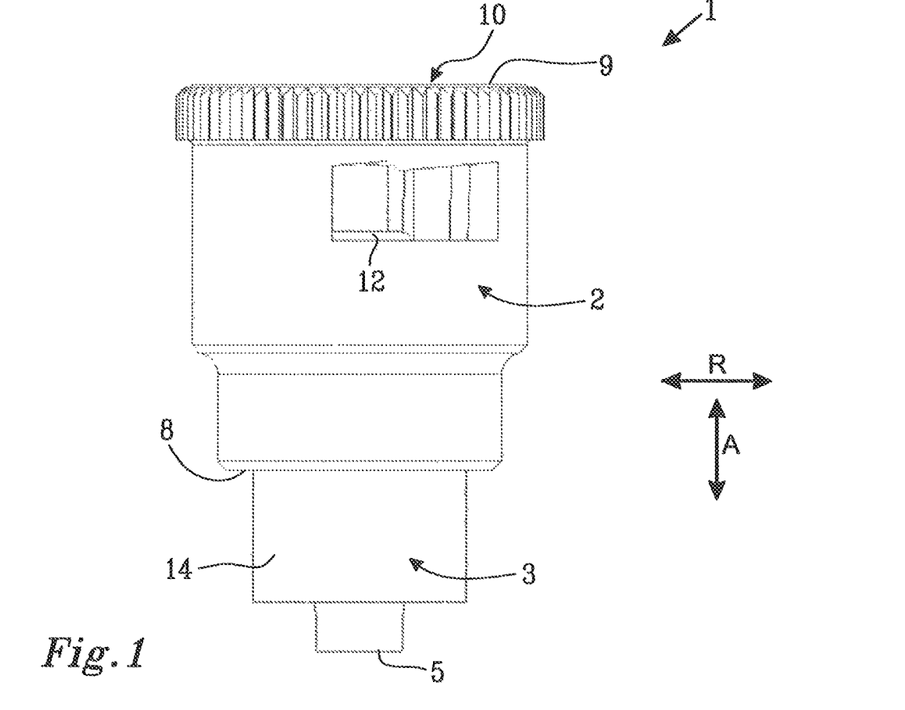
FIG. 1 shows a transfer and connecting device in an in-use configuration.

The inner part is 3 axially movable in the bore 4 in the outer part 2 between a shielding position and a cleaning position. The shielding position is shown in FIG. 1 and in FIGS. 6 and 7 and is also the "in use" position in which the transfer and connecting device 1 is operational and can be used for connecting two medical devices for transferring a fluid between the devices.

In the shielding position, the barrier member 12 is completely withdrawn into the outer part 2 of the transfer and connecting device 1 and is located within the bore 4 in the outer part 2 such that is radially shielded and protected by the walls of the outer part 2. When in the shielding position, the inner part has been moved in relation to the outer part 2 so that the second end 6 of the inner part 3 is located at the first end 8 of the outer part 2 with the first end 5 of the inner part 3 protruding out from the outer part 2 at the first end 8 of the outer part as seen in FIG. 1. This means that when the device 1 is in the operational shielding position, the first end 5 of the inner part 3 forms a first end of the device 1 and the second end 9 of the outer part 2 forms a second, axially opposite end of the device 1. In this configuration, the transfer and connecting device 1 can be connected to a first medical device such as a catheter, a vial, an infusion bag, an IV-set, or another medical coupling device by means of the male connector 20 and the inner thread 21 at the first end 5 of the inner part 3.

Depending on the type of medical device to be coupled to the first end 5 of the inner part and of the device, the connecting means at the first end may be different from the male connector and inner thread shown in the figures. Accordingly, any type of threaded coupling, bayonet fitting, snap-lock, locking ring, slide fitting, clamp, etc., may be used, as known in the art. As illustrated by the embodiment shown in the figures, more than one locking element of the same or different construction may be used in combination to create a coupling between the connecting device 1 and the first medical device. The same considerations apply to the opposite end of the connecting device 1 and the provision of coupling elements for coupling of a second medical device to that end.

When the transfer and connecting device 1 has been connected to a first medical device, it can subsequently be connected with a second medical device carrying a piercing member. The second medical device is connected with the transfer and connecting device 1 at the second end of the outer part 2 and of the transfer and connecting device 1. The second medical device may be a piercing device such as a syringe, another connecting device, a needle protection device, etc.

In the cleaning position, the barrier member 12 is moved to the second end 9 of the outer part 2 by sliding the inner part 3 in the bore 4 in the outer part 2 until the abutting surfaces 17 of the spring struts 15 come into contact with the locking rim 26 at the opening in the outer part 2. In the example shown in the figures, the barrier member is held in the cleaning position by frictional forces. If desired, the device may be provided with one or more element for releasable locking of the barrier member in the cleaning position. Such locking element may be a locking tongue, a locking knob, a locking rim, etc. as known in the art. In the cleaning position, the barrier member 12 is located at least partially outside the outer part 2 of the transfer and connecting device 1 in the axial direction A of the transfer and connecting device 1 and can be easily cleaned before the transfer and connecting device 1 is brought back to the operational shielding position.

Further modifications of the invention within the scope of the claims would be apparent to a skilled person. For instance, the locking and guiding mechanisms disclosed herein may be differently designed and configured without deviating from the invention.

The invention claimed is:

1. A medical transfer and connecting device for connecting a first medical appliance with a second medical appliance, said device having an axial direction and a radial direction and comprising:
an outer part having a first end and a second end with an end opening and a bore extending in said axial direction between said first end and said second end and wherein an inner part carrying a barrier member and having a central canal extending in said axial direction is telescopically arranged in said bore in said outer part, said inner part with said barrier member being axially movable in said bore in said outer part between a shielding position in which said barrier member seals said central canal and is completely located within said bore in said outer part and a cleaning position in which said barrier member seals said central canal and is located with at least a portion of said barrier member extending axially past said end opening in said outer part, wherein, with said barrier member in said shielding position, said end opening is open to receive a medical device.

2. The device in accordance with claim 1, wherein said outer part comprises at least one axially extending groove and said inner part comprises means for sliding engagement with said at least one groove in said outer part.

3. The device in accordance with claim 2, wherein said means for sliding engagement with said at least one groove comprises a spring strut.

4. The device in accordance with claim 3, wherein said spring strut extends towards the second end of the inner part and is slightly outwardly inclined with respect to a central axis through said transfer and connecting device.

5. The device in accordance with claim 2,
wherein said means for sliding engagement with said at least one groove comprises a lug.

6. The device in accordance with claim 5, wherein said groove and said lug form a bayonet fitting between the outer part and the inner part of the transfer and connecting device.

7. The device in accordance with claim 1, wherein said connecting device comprises means for releasably locking said inner part in said shielding position.

8. The device in accordance with claim 7, wherein said means for releasably locking said inner part in said shielding position is a locking knob.

9. The device in accordance with claim 1, wherein said connecting device comprises a lock for releasably locking said inner part in said cleaning position.

10. The device in accordance with claim 1, wherein said device comprises a connection arrangement for connecting said device to a first medical device.

11. The device in accordance with claim 1, wherein said device comprises a connection arrangement for connecting said device to a second medical device, said second medical device comprising a piercing member arranged to pierce said barrier member when said transfer and connecting device is in said shielding position.

12. The device in accordance with claim 10, wherein the inner part includes the connection arrangement.

13. The device in accordance with claim 12, wherein the connection arrangement is positioned within said outer part when said barrier member is in said cleaning position.

* * * * *